(12) United States Patent
Pather et al.

(10) Patent No.: US 7,670,617 B2
(45) Date of Patent: Mar. 2, 2010

(54) SEQUENTIAL DRUG DELIVERY SYSTEMS

(75) Inventors: S. Indiran Pather, Plymouth, MN (US);
John Hontz, Plymouth, MN (US); John M. Siebert, Eden Prairie, MN (US)

(73) Assignee: CIMA Labs Inc., Eden Prairie, MN (US)

( * ) Notice: Subject to any disclaimer, the term of this patent is extended or adjusted under 35 U.S.C. 154(b) by 445 days.

(21) Appl. No.: 10/936,185

(22) Filed: Sep. 8, 2004

(65) Prior Publication Data

US 2005/0031677 A1    Feb. 10, 2005

Related U.S. Application Data

(63) Continuation of application No. 10/623,069, filed on Jul. 18, 2003, now abandoned, which is a continuation of application No. 09/901,983, filed on Jul. 10, 2001, now abandoned.

(51) Int. Cl.
*A61F 9/02* (2006.01)

(52) U.S. Cl. ......................... 424/448; 424/400

(58) Field of Classification Search ............... 424/448, 424/400
See application file for complete search history.

(56) References Cited

U.S. PATENT DOCUMENTS

| | | | |
|---|---|---|---|
| 3,131,123 A | | 4/1964 | Masquelier |
| 4,443,428 A | * | 4/1984 | Oshlack et al. ............ 424/457 |
| 4,452,808 A | * | 6/1984 | Gallagher, Jr. ............ 514/418 |
| 4,756,710 A | | 7/1988 | Bondi et al. |
| 5,102,666 A | * | 4/1992 | Acharya .................... 424/487 |
| 5,178,878 A | | 1/1993 | Wehling et al. |
| 5,387,420 A | | 2/1995 | Mitchell et al. |
| 5,445,827 A | * | 8/1995 | Fritsch et al. ............. 424/466 |
| 5,503,846 A | | 4/1996 | Wehling et al. |
| 5,607,697 A | | 3/1997 | Alkire et al. |
| 5,624,687 A | | 4/1997 | Yano et al. |
| 5,626,866 A | | 5/1997 | Ebert et al. |
| 5,807,688 A | * | 9/1998 | Blackburn et al. .......... 435/7.6 |
| 5,853,748 A | | 12/1998 | New |

(Continued)

FOREIGN PATENT DOCUMENTS

EP    0 197 504 A1    10/1986

(Continued)

OTHER PUBLICATIONS

Weinberg et al., "Sublingual absorption of selected opioid analgesics", Clinical Pharmacology and Therapeutics, Sep. 1988, 44(3), pp. 335-342.

(Continued)

*Primary Examiner*—M P Woodward
*Assistant Examiner*—Aradhana Sasan
(74) *Attorney, Agent, or Firm*—Woodcock Washburn LLP

(57) ABSTRACT

The invention relates to methods and composition for improving absorption and dissolution of active ingredients of drugs. The invention provides a method of administration of an active ingredient to a mammal through a transmucosal route that includes delivering the active ingredient to a desired site in a body of the mammal, and, sequentially, at the desired site, promoting dissolution and absorption of the active ingredient. In a preferred embodiment, the pH of the localized environment of the active ingredient is sequentially modified to promote dissolution and absorption.

11 Claims, 2 Drawing Sheets

U.S. PATENT DOCUMENTS

| | | | |
|---|---|---|---|
| 5,900,252 | A | 5/1999 | Calanchi et al. |
| 5,952,004 | A | 9/1999 | Rudnic et al. |
| 6,034,085 | A | 3/2000 | Joshi et al. |
| 6,068,853 | A | 5/2000 | Giannos et al. |
| 6,117,912 | A | 9/2000 | DiSanto |
| 6,200,604 | B1 * | 3/2001 | Pather et al. ............... 424/466 |
| 6,242,002 | B1 | 6/2001 | Tritthart et al. |
| 6,264,981 | B1 | 7/2001 | Zhang et al. |
| 6,312,728 | B1 * | 11/2001 | Beiman et al. ............ 424/490 |
| 6,326,360 | B1 | 12/2001 | Kanazawa et al. |
| 6,326,384 | B1 | 12/2001 | Whittle et al. |
| 6,350,470 | B1 | 2/2002 | Pather et al. |
| 6,391,335 | B1 | 5/2002 | Pather et al. |
| 6,509,036 | B2 | 1/2003 | Pather et al. |
| 6,641,838 | B2 | 11/2003 | Pather et al. |
| 6,764,696 | B2 | 7/2004 | Pather et al. |
| 6,974,590 | B2 | 12/2005 | Pather et al. |
| 2005/0037072 | A1 | 2/2005 | Pather et al. |
| 2005/0142197 | A1 | 6/2005 | Moe et al. |
| 2005/0142198 | A1 | 6/2005 | Moe et al. |
| 2005/0163838 | A1 | 7/2005 | Moe |
| 2005/0169989 | A1 | 8/2005 | Moe et al. |
| 2006/0292219 | A1 | 12/2006 | Pather et al. |
| 2007/0036853 | A1 | 2/2007 | Agarwal et al. |

FOREIGN PATENT DOCUMENTS

| | | |
|---|---|---|
| EP | 0 354 973 B2 | 2/1990 |
| EP | 1067905 | 10/1999 |
| EP | 1 062 952 A | 12/2000 |
| JP | 7-277959 | 10/1995 |
| WO | WO-91/04757 | 4/1991 |
| WO | 95/07701 | 3/1995 |
| WO | WO-95/34291 | 12/1995 |
| WO | WO-96/29993 | 10/1996 |
| WO | WO-97/17067 | 5/1997 |
| WO | WO-99/45934 A | 9/1999 |
| WO | WO-99/49842 | 10/1999 |
| WO | WO-00/09093 A | 2/2000 |
| WO | WO-00/35418 | 6/2000 |
| WO | 00/59423 | 10/2000 |
| WO | WO 00/66089 A1 | 11/2000 |

OTHER PUBLICATIONS

Streisand et al., "Buccal absorption of fentanyl is pH-dependent in dogs", Anesthesiology, (Mar. 1995), 82 (3), pp. 759-764.

Chen et al., "Studies on formulations of fentanyl buccal adhesive tablets", Zhonggup Yiyao Gongye Zazhi, 1997, 28 (3), 129-131.

Supplementary European Search Report, EP 00 92 6341, Dated Nov. 23, 2005.

Mechanistic Studies on Effervescent-Induced Permeability Enhancement by Jonathan D. Eichman, a dissertation submitted in partial fulfillment of the requirements for the degree of Doctor of Philosophy (Pharmacy) at the University of Wisconsin-Madison 1997.

Ranade, V.V.; Drug Delivery Systems Part 5B. Oral Drug Delivery, The Journal of Clinical Pharmacology, Feb. 1991, pp. 98-115, vol. 31.

Giannos, S.A.; Dinh, S.M.; Berner, B.; Temporally Controlled Drug Delivery Systems: Coupling of pH Oscillators with Membrane Diffusion, Journal of Pharmaceutical Sciences, May 1995, pp. 539-543, vol. 84, No. 5.

Amighi, K.; Timmermans, J.; Puigdevall, J.; Baltes, E.; Moës, A.. J.; Peroral Sustained-Release Film-Coated Pellets as a Means to Overcome Physicochemical and Biological Drug-Related Problems. I. In Vitro Development and Evaluation, Drug Development and Industrial Pharmacy, 1998, pp. 509-515, vol. 24, No. 6.

Sorasuchart, W.; Wardrop, J.; Ayers, J.; Drug Release from Spray Layered and Coated Drug-Containing Beads: Effects of pH and Comparison of Different Dissolution Methods, Drug Development and Industrial Pharmacy, 1999, pp. 1093-1098, vol. 25, No. 10.

Berko, S.; Regdon Jun, G.; Erös, I.; Influence of pH Change on Drug Release from Rectal Suppositories, Die Pharmazie, Apr. 2000, p. 324, vol. 55., Govi-Verlag Pharmazeutischer Verlag GmbH, Eschborn.

Streubel, A.; Siepmann, J.; Dashevsky, A.; Bodmeier, R.; pH-Independent Release of a Weakly Basic Drug from Water-Insoluble and -Soluble Matrix Tablets, Journal of Controlled Release, 2000, pp. 101-110, vol. 67.

U.S. Appl. No. 09/661,693, filed Sep. 14, 2000.

Rowe et al., Handbook of Pharamceutical Excipients, 2006, Fifth Edition, pp. 758-759.

http://chemicalland21.com/industrialchem/inorganic/SODIUM%20SULPHATE.htm, Sodium Sulphate, 2 pages.

Stanley et al, "Novel Delivery Systems: Oral Transmucosal and Intranasal Transmucosal", Journal of Pain and Sympton Management, vol. 7, No. 3, Apr. 1992, pp. 163-171.

Hessel, P.G., et al., "A Comparison of the availability of prochlorperazinc following i.m. buccal and oral administration", International Journal of Pharmaceutics, Jun. 1, 1989, vol. 52, Issue 2, p. 159-164.

Office Action from corresponding European Application 04 815 715.

* cited by examiner

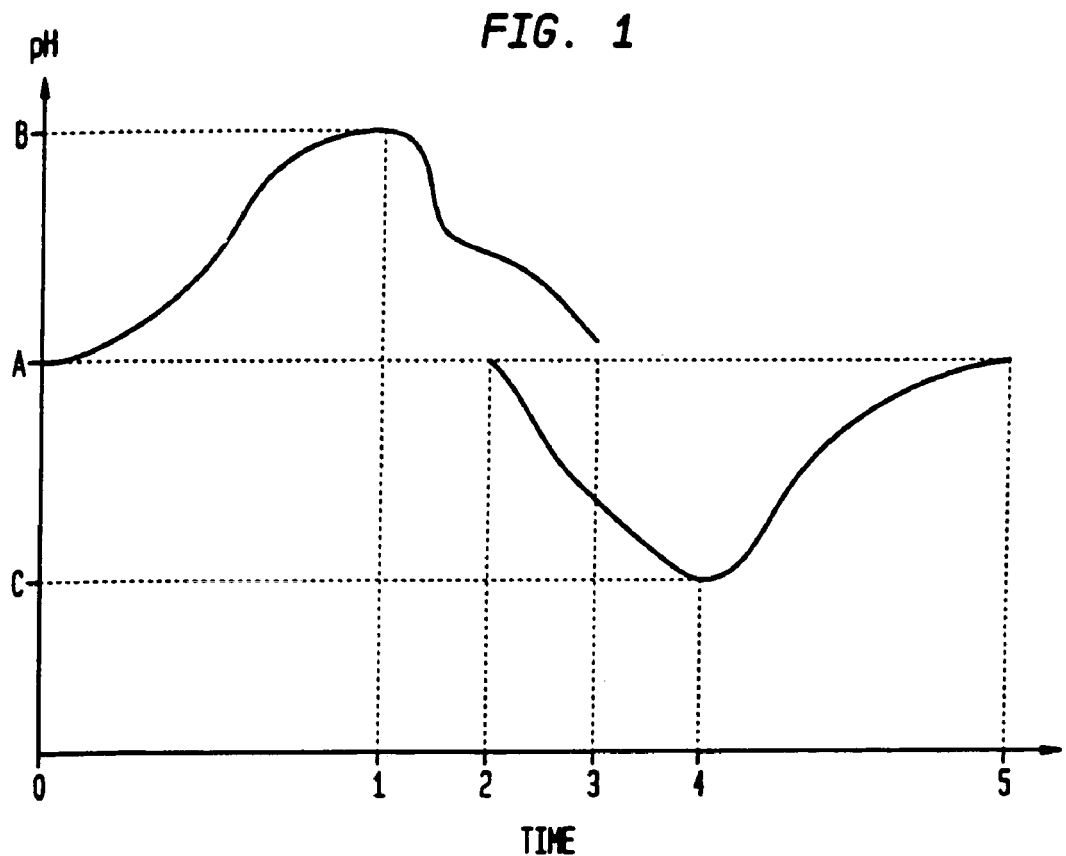
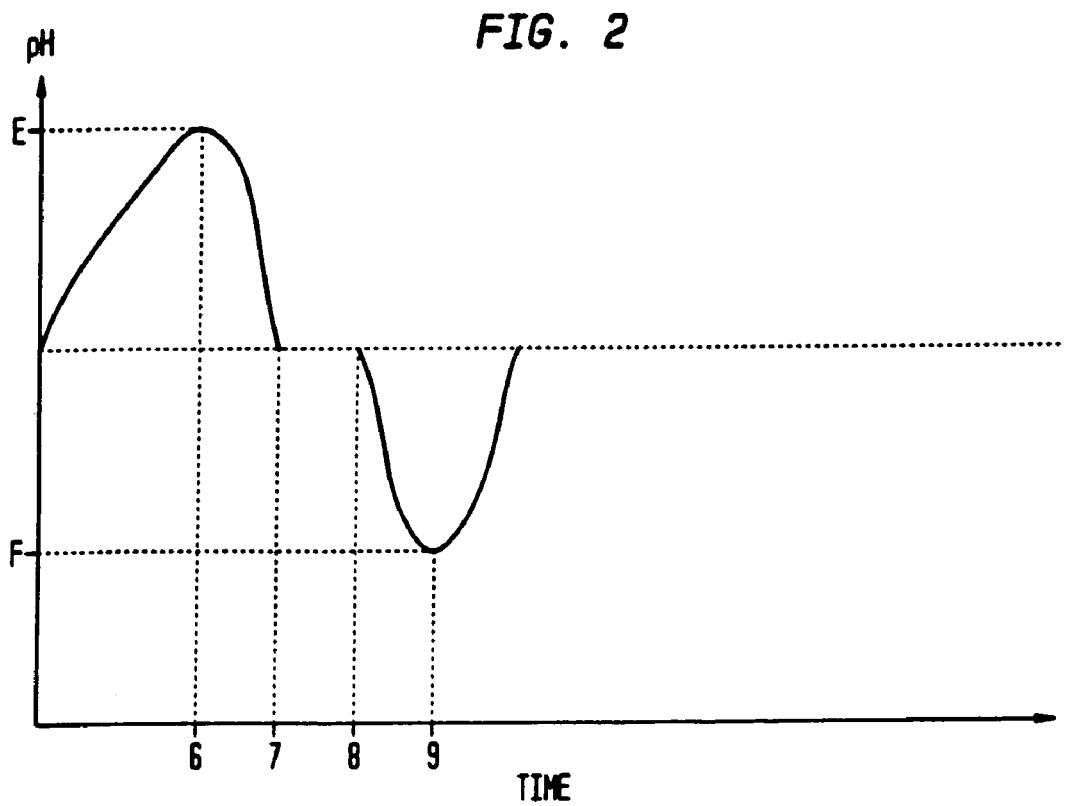

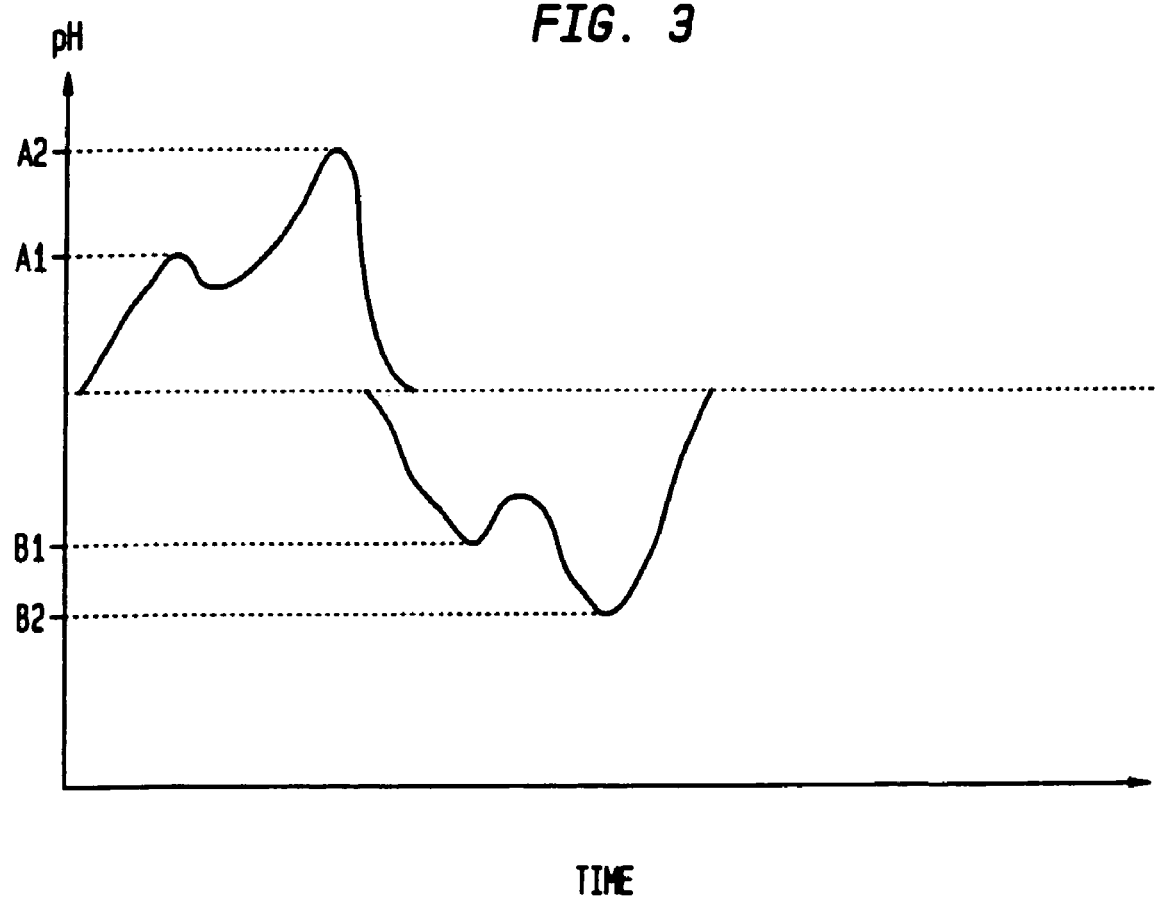

SEQUENTIAL DRUG DELIVERY SYSTEMS

CROSS REFERENCE TO RELATED APPLICATIONS

The present application is a continuation of U.S. patent application Ser. No. 10/623,069, filed Jul. 18, 2003, which is a continuation of U.S. patent application Ser. No. 09/901,983, filed Jul. 10, 2001, incorporated herein by reference in their entirety.

FIELD OF THE INVENTION

The present invention relates to pharmaceutical compositions and methods for enhancing bioavailability of active ingredients, and more particularly to pharmaceutical compositions for enhancing dissolution and absorption of active ingredients.

BACKGROUND OF THE INVENTION

The development of methodologies for enhancing dissolution and absorption of active ingredients is a major field of pharmaceutical formulation research. As generally defined, dissolution is the rate and extent to which an active ingredient enters into solution. Absorption is generally defined as the rate and extent to which the active ingredient moves from its site of administration to the site of action or general circulation. Absorption usually involves a passive diffusion of the active ingredient across a mucosal membrane.

Although in a few rare instances, very fine, non-dissolved particles may be absorbed into the body of a mammalian subject by special processes, most often active ingredients must dissolve before absorption can take place. However, in formulating pharmaceutical compositions, the goals of rapid absorption and dissolution of active ingredients are often difficult to reconcile. Thus, the environment that favors dissolution may sometimes inhibit absorption and vice versa.

Good examples of this often-competing relationship may be found in studying the influence of pH, which is the measure of concentration of the $H^+$ ions, on dissolution and/or absorption of active ingredients. Many formulation techniques focus on the pH of the pharmaceutical compositions and dosage forms, and/or the pH environment at various sites in the body. However, even though pH is often important, standard pharmaceutical practice views the pH requirements for dissolution and absorption as somewhat contradictory. For example, Physical Pharmacy by Alfred Martin, Lea and Febiger, 4th Ed. (1993) teaches that a lower pH enhances the dissolution of weakly basic drugs while a higher pH enhances their absorption. Thus, the standard pharmaceutical practice often involves selecting a pharmaceutical dosage form with a pH that is a compromise between the pH that favors dissolution and the pH that favors absorption. Alternatively, the pH is selected to favor either the dissolution or the absorption, whichever is considered to be the rate-determining step in delivering the drug to its site of action.

The drugs that benefit from such pH adjustments are usually weakly basic or weakly acidic compounds. They make up a large proportion of available drugs and fall into numerous therapeutic classes. Usually, the drugs are delivered in either liquid or solid form. With respect to liquid pharmaceutical preparations, the pH of the liquid may be directly adjusted prior to administration to achieve the desired degree of dissolution of the active ingredient. With respect to the solid drug delivery vehicles such as the dosage forms, the dissolution typically takes place in vivo, and the modification of the pH is usually achieved by selecting the content of the dosage form. For example, an appropriate salt form of the drug may be used to improve the dissolution. In both modes of administration, however, the selected pH is rarely optimal for both dissolution and absorption of the active ingredient.

Therefore, there is a need for a method of administration that facilitates both absorption and dissolution of active ingredients.

SUMMARY OF THE INVENTION

This need is addressed by the methods and the compositions of the present invention.

According to one aspect, the present invention provides a method of administration of an active ingredient to a mammal through a transmucosal route by delivering the active ingredient to a desired site in a body of the mammal, and then sequentially promoting dissolution and absorption of the active ingredient at the desired site. Preferably, the active ingredient is delivered to the desired site in the dosage form having a first portion and a second portion. At the desired site, the first portion of the dosage form is released to promote dissolution of the active ingredient followed by the release of the second portion of the dosage form to promote the absorption of the active ingredient. The desired site may include the site of administration and the site of absorption.

Preferably, the first portion of the dosage form includes one or more first substances that promote the dissolution of the active ingredient and one or more second substances that promote its absorption. The first substances may include pH-adjusting substances, surface-active compounds, pharmaceutically acceptable solvents, and enveloping additives. The second substances may include pH adjusting substances, effervescent penetration enhancers, non-effervescent penetration enhancers, and bioadhesives.

In a preferred embodiment, the first portion of the dosage form includes a first pH adjusting substance or substances so that the active ingredient attains a first state of dissociation that promotes its dissolution and a second portion of the dosage form includes a second pH-adjusting substance or substances so that the active ingredient attains a second state of dissociation that promotes absorption.

According to another aspect, the invention provides a method for administering an active ingredient by a transmucosal route in a mammal including administering the active ingredient in the dosage form with a first pH-adjusting substance and a second pH-adjusting substance so that the first pH-adjusting substance attains peak activity in the localized environment of the active ingredient before the second pH-adjusting substance. The localized environment of the active ingredient attains a first pH and then a second pH, with the first pH promoting dissolution of the active ingredient and the second pH promoting absorption of the active ingredient. The first and second pH adjusting substances may be, respectively, an acid and a base, a base and an acid, a base and a base, or an acid and an acid.

According to another aspect, the invention provides a pharmaceutical composition including an active ingredient in a dosage form having a first portion, a second portion, and means for sequential release of the first portion and the second portion of the dosage form at a desired site. Preferably, the first portion of the dosage form may include one or more first substances that promote dissolution of the active ingredient and one or more second substances that promote its absorption. Preferably, the first substance is a first pH-adjusting substance and the second substance is a second pH-adjusting substance; and the means for sequential release are means for sequentially controlling the activity of the pH-adjusting substances. The activity of the pH-adjusting substances is controlled so that the first pH-adjusting substance attains peak activity in the localized environment of the active ingredient before the second pH-adjusting substance. Thus, the localized environment of the active ingredient attains a first pH and then a second pH, with the first pH promoting dissolution of the active ingredient and the second pH promoting its absorption. In this embodiment, the one or more first substances may be pH-adjusting substances or dissolution enhancers, whereas the one or more of the second substances may be pH-adjusting substances, effervescent penetration enhancers or non-effervescent penetration enhancers.

Preferably, in accordance with the invention, a variety of active ingredients may be administered, such as analgesics, anti-inflammatories, antipyretics, antibiotics, antimicrobials, laxatives, anorexics, antihistamines, antiasthmatics, antidiuretics, antiflatulents, antimigraine agents, antispasmodics, sedatives, antihyperactives, antihypertensives, tranquilizers, decongestants, beta blockers, peptides, proteins, and oligonucleotides. The route of administration may include buccal, sublingual, gingival, gastrointestinal, rectal, vaginal, and nasal routes.

When the active ingredient is administered in the dosage form, the dosage form may also include means for sequential release of the first and second portions, including such means as coatings, membranes, matrix materials, pre-cursors of active ingredients and pre-cursors of pH-adjusting substances. In one variant, the second portion of the dosage form may include the second pH-adjusting substance dispersed in a controlled matrix material. In another variant, the first portion of the dosage form may include the active ingredient. In another variant, the second portion of the dosage form may include the second pH-adjusting substance surrounded by a coating so that the first pH-adjusting substance is peripheral to the coating in the dosage form. In yet another variant, the active ingredient may be peripheral to the coating in the dosage form. In yet another variant, the second portion of the dosage includes the second pH-adjusting substance surrounded by a membrane with the first pH-adjusting substance being peripheral to the membrane. In this variant, the active ingredient may be peripheral to the membrane.

DETAILED DESCRIPTION OF THE DRAWINGS

FIG. 1 is a schematic pH/time profile of dissolution/absorption of a weakly acidic active ingredient in accordance with a preferred embodiment of the invention;

FIG. 2 is another schematic pH/time profile of dissolution/absorption of an active ingredient in accordance with a preferred embodiment of the invention;

FIG. 3 is a schematic pH/time profile of dissolution/absorption of an active ingredient that utilizes a combination of pH-adjusting substances in accordance with a preferred embodiment of the invention.

DETAILED DESCRIPTION OF THE INVENTION

The present invention provides that the often-competing goals of improving dissolution and absorption of active ingredients may be addressed by sequentially promoting dissolution and absorption of an active ingredient at a desired site. Preferably, the localized environment of the active ingredient is sequentially modified to sequentially create favorable conditions for its dissolution and absorption.

The localized environment may include the contents and fluids at the site of drug administration, drug release or drug absorption which are in immediate contact with or which immediately surround the active ingredient in a dosage form or composition, as well as any portion of the active ingredient dissolved or separated from the dosage form or composition during the processes of administration, release from the dosage form or dissolution into the body fluids. The localized environment may also include any liquid that has penetrated into the dosage form or composition, or which immediately surrounds the dosage form or composition.

In accordance with the invention, any method or mechanism of modifying the localized environment of an active ingredient may be used. The methods and mechanisms suitable to promote dissolution in accordance with the invention may include, for example, pH control in the localized environment of the active ingredient and/or the use of various dissolution enhancing substances, such as surface-active compounds, pharmaceutically-acceptable solvents, various enveloping additives, and others, including methods and mechanisms known to those skilled in the art. The methods and mechanisms suitable to promote absorption of an active ingredient include pH control, use of penetration enhancers, both effervescent and non-effervescent, bioadhesives, and others, including methods and mechanisms known to those skilled in the art.

The sequential modification of the localized environment is especially desired when the goals of promoting dissolution and absorption compete, for example, when the changes in the localized environment that tend to promote dissolution inhibit absorption and vice versa, as is often observed with respect to pH modifications. According to the preferred embodiment of the invention, the sequential modification of the localized environment involves sequential pH adjustment. According to this embodiment, the invention provides a sequential pH-adjusting system that may promote and preferably promotes at least two pH changes at the site of drug release, the site of administration, the site of absorption, or at multiple sites. Preferably, the pH-adjusting system promotes the at least two pH adjustments at or near the site of absorption of the active ingredient, the extent of the adjustments preferably being within the limits tolerable to the subject of the administration.

The sequential pH-adjusting system preferably includes two or more pH-adjusting substances, which are selected and controlled to attain their peak activities at different times. The sequential release or activation of the pH-adjusting substances sequentially lowers and/or raises the pH of the localized environment. When released at the site of administration or the site of absorption, the pH-adjusting substances sequentially produce at least two pH adjustments in the localized environment of the active ingredient. A first pH-adjusting substance causes the first pH adjustment that promotes dissolution of the active ingredient, and a second pH-adjusting substance causes the second pH adjustment that promotes absorption. Each pH adjustment may also be produced by a combination of pH-adjusting substances. Thus, the first pH adjustment may involve the use of more than one pH-adjusting substances, released simultaneously with each other or at different times to promote dissolution. Similarly, the second pH adjustment may also include the use of more than one pH-adjusting substance.

As used herein, the activity of a pH-adjusting substance may be the overall activity during administration, including the total pH adjustment caused by a pH-adjusting substance. The peak activity of a pH-adjusting substance refers to the greatest magnitude of the pH adjustment in the localized environment produced by the pH-adjusting substance.

Although the present invention is not limited to any particular theory of operation, the following discussion is presented to illustrate the operation of one embodiment of the invention. As discussed above, many active ingredients are weak acids or bases, and thus are believed to exist in equilibrium between unionized and ionized forms. For example, for weakly acidic active ingredient HA, the dissociation equation may be schematically represented as follows:

$$HA \rightleftharpoons H^+ + A^-,$$

where HA is the unionized form, $A^-$ is the ionized form, and $H^+$ is a proton. In most cases, the solubility of the unionized form is much lower than the solubility of the ionized form of the active ingredient. Thus, the degree of dissociation often controls the dissolution of active ingredients. In other words, the higher the relative proportion of the ionized form ($A^-$) relative to the proportion of unionized form (HA), the higher the extent of the dissolution.

At the same time, by definition, weak acids are believed to dissociate to a rather small degree, i.e., the relative concentration of the ionized form is usually relatively low. Further, the rate of dissociation is proportional to the concentration of the unionized form (HA) in the solution. The rate of the reverse process of association is proportional to the concentration of the ionized form $A^-$ and the concentration of the protons $H^+$. In accordance with the Le Chatelier principle, the addition of external acid (a source of $H^+$) shifts the equilibrium to the left, thus decreasing the extent and the rate of dissociation. Thus, addition of external acid to a solution of a weakly acidic active ingredient is likely to inhibit dissolution. In contrast, the addition of an external base shifts the equilibrium to the right and promotes dissolution.

Therefore, in administering a weakly acidic active ingredient, the first pH-adjusting substance preferably has a basic nature to promote the dissolution of the acidic active ingredient by raising the pH of the localized environment, shifting the equilibrium to the right and thus converting a greater percentage of the active ingredient to the ionized form ($A^-$) than would be the case at normal physiological pH.

On the other hand, the mucosal membrane (or mucosa) is generally thought to be relatively hydrophobic in comparison with the essentially aqueous and thus hydrophilic dissolution media of various body cavities. Thus, a unionized form of the active ingredient, which is typically more hydrophobic than the charged ionized form, may be better absorbed across the mucosal membrane, especially via certain specific transmucosal routes such as the cell membrane route (so-called transcellular absorption). Therefore, for weakly acidic active ingredients, the second pH-adjusting substance preferably has an acidic nature to lower the pH of the localized environment, shifting the equilibrium to the left and thus converting a greater percentage of the active ingredient to the unionized form (HA) than would be the case at normal physiological pH.

Likewise, for a weakly basic active ingredient, the dissociation equations may be schematically represented as

$$BOH \rightleftharpoons B^+ + OH^- \quad \text{or}$$
$$B + H^+ \rightleftharpoons BH^+,$$

depending on the structure of the active ingredient; where BOH and B are the unionized forms of the active ingredient, $B^+$ and $BH^+$ are the ionized forms of the active ingredient, and $OH^-$ is a hydroxyl ion. Addition of an external base shifts the equilibrium to the left, either by providing a source of $OH^-$ ions or by consuming the protons. On the other hand, addition of an external acid shifts the equilibrium to the right.

Thus, in administering a weakly basic active ingredient, the first pH-adjusting substance preferably has an acidic nature to promote the dissolution of the active ingredient by lowering the pH of the localized environment, shifting the equilibrium to the right and thereby converting a greater percentage of the active ingredient to an ionized form(s) ($B^+$ or $BH^+$) than in the absence of the pH adjustment. The second pH-adjusting substance preferably has basic nature to promote absorption of the active ingredient across the mucosa by raising the pH of the localized environment, shifting the equilibrium to the left and thereby converting a greater percentage of the active ingredient to the unionized form(s) (BOH or B)

A sequential release of the pH-adjusting substances may therefore be used to adjust the pH of the localized environment within a certain pH range. Although for most active ingredients it is preferred to first promote the shift in the dissociation equilibrium toward the ionized form and then the unionized form, the sequence of the pH adjustments may vary. Depending on the dissolution and absorption profiles of the desired active ingredient, the sequential pH-adjusting system of the invention may also produce pH adjustments that favor only the ionized form or only the unionized form of the active ingredient (e.g., when different concentration of either form is favored for both dissolution and absorption). The sequence of pH adjustments may also be reversed, if desired.

Various mechanisms may be responsible for promoting the sequential dissolution and absorption according to the invention. According to one embodiment of the invention, the primary mechanism is believed to involve pH control over the relative concentrations of ionized and unionized forms of the active ingredient. However, other mechanisms may also be implicated. These mechanisms may include, for example, reduction in the thickness and/or viscosity of the mucus layer, changes in the structure of the cell membrane, increase in the hydrophobicity within the cellular membranes, alteration of tight junctions, ion pairing and complexation or other chemical modifications, enhancement of active transport mechanisms; modification of the cellular efflux mechanisms, changes in the stability of active ingredients toward enzymes or other factors at the site of administration or absorption, and the like.

The activity of the first pH-adjusting substance may overlap with the activity of the second pH-adjusting substance. However, preferably, the peak activity of the first pH-adjusting substance does not coincide with the peak activity of the second pH-adjusting substance. Otherwise, it may not be possible to produce the at least two pH adjustments described above.

With reference to FIG. 1, the initial pH of the localized environment is A. Typically, A is the physiological pH at the site of dissolution of the active ingredient. Upon release of the first pH-adjusting substance (a base) at the time 0, the pH of the localized environment increases until the first pH-adjusting substance reaches its peak activity B at the time 1. The second pH-adjusting substance (an acid) is released at the time 2. At the time 2, the first pH-adjusting substance is still active in the localized environment of the active ingredient. Therefore, at the time 2, the activities of the first and second pH-adjusting substances overlap. The overlap ends at the time 3. At the time 4, the second pH-adjusting substance reaches its peak activity C. At the time 5, the activity of the pH-adjusting system ends. Preferably, at the time 5, the absorption of the active ingredient is complete.

As seen from FIG. 1, while there may be some overlap between the activities of the pH-adjusting substances, the peak activity B of the first pH-adjusting substance preferably occurs prior to the peak activity C of the second pH-adjusting substance. The time difference between the peak activities of the pH-adjusting substances (e.g., with reference to FIG. 1, time 4 minus time 1), the time difference between the end of activity of the first pH-adjusting substance and the release of the second pH-adjusting substance (e.g., time 2 minus time 3), and other pH/time profile parameters are matters of formulation design, and depend on many factors. Preferably, the times of release and peak activity of the second pH-adjusting substance are selected to permit the dissolution of a substantial portion of the active ingredient prior to the release of the second pH-adjusting substance. At the same time, the time differences are preferably small so that the shift to the more absorbable species occurs as soon as possible. Thus, the overlap shown in FIG. 1 may be commonly observed.

However, the overlap between the activities of the first and the second pH-adjusting substances is not required. Referring to FIG. 2, the first pH-adjusting substance reaches its peak activity E at the time 6 and ends its activity at the time 7. The second pH-adjusting substance is released at the time 8 and reaches its peak activity F at the time 9. The peak activities E and F do not coincide. Also, the end of activity for the first pH-adjusting substance (7) is earlier than the release of the second pH-adjusting substance (8). Thus, no overlap is observed.

As described above, the actual time differences between the first and second pH adjustments depends on many factors, for example the rate of release and dissolution of the active ingredient, the fluid turnover rate of the body cavity, and the buffer capacity of the body fluid. For example, a smaller time difference may be needed for sublingual than for rectal administration, mainly due to a faster production of saliva than of rectal fluids and the fact that the flow of saliva tends to remove the drug from the zone of absorption. Preferably, the time difference between the release of the first pH-adjusting substance and the second pH-adjusting substance is from about 30 seconds to about 60 minutes. More preferably, the time difference is from about 3 to about 15 minutes.

For active ingredients that have a naturally slow rate of dissolution and/or absorption, the time difference is likely to be more prolonged. When the concentration of the unionized form of an active ingredient is larger than its solubility at a given pH, the active ingredient may, in principle, precipitate out of solution. Thus, rapid conversion of the ionized form of the active ingredient into the unionized form may be undesirable. In relation to the present invention, however, absorption of the active ingredient into biological tissues removes the unionized form from solution, thus reducing its concentration and the likelihood of precipitation. Nevertheless, when the rate of absorption for a particular active ingredient is known to be slow, the rate of release of the second pH-adjusting substance may need to be reduced to control the rate of formation of the unionized species.

If desired, organic solvents may be incorporated in the dosage form to further reduce the risk of precipitation. The additional solvents may include for example ethanol and other alcohols, polyethylene glycol, propylene glycol, isopropyl myristate, glycerin and other pharmaceutically acceptable solvents. Commercial solvents or solvent blends designed to increase solubility of chemical substances for human use may also be included. An example of such a commercial product is Arlasolv™. The additional solvents are more easily incorporated into liquid dosage forms or dosage forms that are converted to a liquid state immediately before use. For example, a tablet or powder for reconstitution may be supplied with the liquid for reconstituting the dosage form.

It is highly preferred that the pH adjustments be tolerable to the subject of drug administration. Thus, large changes in the pH of body fluids are often undesirable. For example, such changes may result in the irritation to the tissues adjoining the localized environment of the active ingredient. Also, the pH adjustments beyond one pH unit generally provide smaller or non-existent further improvement in dissolution and/or absorption over that provided by a pH adjustment of 1 pH unit. Therefore, pH adjustments of about one pH unit (e.g., one pH unit above the $pK_a$ of the active ingredient and/or one pH unit below the $pK_a$) are preferred. However, there may be instances when pH adjustments of less than one pH unit would be preferred, for example, to decrease irritation of sensitive tissues or based on the dissolution and absorption profile for a particular active ingredient. Similarly, larger adjustments may also be used where appropriate and/or advantageous.

Stepwise pH adjustments may also be desirable. To this end, the first and/or second pH adjustments may each include a series of pH adjustments to promote dissolution and/or absorption. This may be accomplished, for example, by sequential activation of two or more pH-adjusting substances to promote dissolution, and/or sequential activation of two or more pH-adjusting substances to promote absorption. As shown in FIG. 3, when combinations of pH-adjusting substances are employed to promote dissolution (A1 and A2) and/or absorption (B1 and B2), the peak activities of the pH-adjusting substances employed to promote dissolution (A1 and A2) preferably do not overlap with peak activities of the pH-adjusting substance employed to promote absorption (B1 and B2).

Various methods are used to select the desired magnitude (s) of pH adjustments, and the requisite amounts of the pH-adjusting substances. According to the Henderson-Hasselbach equation, the ratio of the ionized (I) and unionized (U) forms of the active ingredient ([I]/[U]) is a function of the solution pH of the localized environment and the $pK_a$ of the active ingredient. For example, for a weakly acidic active ingredient HA

$$HA \rightleftharpoons H^+ + A^-,$$

the Henderson-Hasselbach equation is $$pK_a - pH = \log\frac{[HA]}{[A^-]},$$

where [HA] is the concentration of the unionized (U) form, and [A$^-$] is the concentration of the ionized (I) form of the active ingredient. In accordance with the Henderson-Hasselbach equation, a change of one unit in the pH of the localized environment is believed to shift the equilibrium between the ionized (I) and unionized (U) forms of the active ingredient by a factor of 10. For example, if the initial ratio [HA]/[A$^-$] before pH adjustment of one pH unit was 1:1, the ratio after the adjustment is evaluated to be approximately 10:1 or 1:10, depending on the direction of the adjustment.

Thus, knowing the $pK_a$ of the active ingredient and the desired degree of its dissociation ([A⁻]) and/or association ([HA]), it is possible to evaluate the desired pH of the localized environment, and hence to estimate the requisite amount (s) of appropriate pH-adjusting substance(s). Similar calculations may be also carried out for basic active ingredients.

Preferably, the total range of the pH adjustments, including the first and the second pH adjustments, is selected to place the $pK_a$ of the active ingredient at the center of the adjustment range. As explained above, large pH adjustments are not preferred, and may not be required.

The amounts of necessary pH-adjusting substances may also be determined, for example, by using suitable in vitro dissolution and absorption models. For example, the amount of a pH-adjusting substance necessary to promote dissolution may be determined by placing a dosage form or a composition containing a specific amount of the pH-adjusting substance into a liquid dissolution medium. The preferred liquid medium has a buffer capacity and a pH similar to the body fluid it emulates. The liquid media is then stirred to simulate dissolution in the selected body fluid. As the dissolution of the dosage form or composition progresses, the pH of the liquid media is measured at several time points. The dissolution of the active ingredient is assessed, for example, by visual inspection or by chemical means (e.g., quantitative HPLC, NMR, IR or the like). Similar formulations containing varying amounts of pH-adjusting substance are made and tested in the same manner. The collected pH/time dissolution profiles at different amounts of the pH-adjusting substance become the basis for evaluating the particular formulations. Preferably, the amount of the pH-adjusting substance that leads to the desired magnitude of pH adjustment, optimal pH/time profile and rate of dissolution is chosen for formulating the active ingredient.

Suitable in vitro absorption models may also be used to evaluate the amounts of the second pH-adjusting substances. For example, tissue cultures, such as rat or rabbit intestinal tissue, and artificial membranes bathed in solutions, which simulate the pH and the buffer capacity at the site of absorption, may be used as in vitro absorption models. In determining the amounts of the second pH-adjusting substances, it may be necessary to consider the pH effects of the first pH adjustment or adjustments.

In practice, the amounts of the pH-adjusting substances are usually initially estimated on a theoretical basis, using calculations based on the Henderson-Hasselbach equation or similar theoretical expressions described in standard pharmaceutical science textbooks, for example, Physical Pharmacy by Alfred Martin, Lea and Febiger, 4th Ed. (1993), and then fine-tuned by experimentation.

The pH-adjusting substances may include any agent that promotes pH adjustments in mammals. Preferably the pH-adjusting substances are acids and bases, acid and base derivatives, and other chemicals that convert to acids and/or bases in vivo, and are safe for use in mammals. More preferably, the pH-adjusting substances are weak acids and/or weak bases. Suitable weak acids include, for example, food acids, such as citric, tartaric, amalic, fumeric, adipic, succinics and combinations thereof. Suitable weak bases include, for example, carbonate sources, preferably sodium bicarbonate, sodium carbonate, potassium bicarbonate and potassium carbonate, magnesium carbonate and combinations thereof. The pH-adjusting substances may also include precursors that convert to acids or bases in vivo, including precursors that are sequentially activated in accordance with properties of the localized environment.

To achieve the sequential modification of the localized environment, the active ingredient is preferably included in a dosage form or composition. In accordance with one embodiment, the invention provides that the active ingredient may be administered by delivering it, in a dosage form, to a desired site and then sequentially releasing a first portion of the dosage form to promote the dissolution of the active ingredient, followed by a second portion of the dosage form to promote absorption. To effect the sequential release of the first and second portions of the dosage form, various mechanisms and methods may be used. The means of sequential release may include, for example, coatings, membranes, and matrix materials.

In a preferred embodiment, the pH-adjusting substances and the active ingredient are combined with one or more coatings to sequentially control their release. For example, an uncoated active ingredient and an uncoated first pH-adjusting substance may be combined in a dosage form with a coated second pH-adjusting substance. The coating may substantially surround the second pH-adjusting substance. After administration, the first pH-adjusting substance and the active ingredient are included in the first portion of the dosage form to be released. The first pH-adjusting substance causes the desired change in the pH of the localized environment of the active ingredient. Initially, the coating surrounding the second pH-adjusting substance prevents or limits its release. Subsequently, when the coating surrounding the second pH-adjusting substance dissolves or is removed, the second portion of the dosage form that includes the second pH-adjusting substance is released, promoting the desired second pH change.

Two or more coatings having varying properties and/or thickness may also be utilized. For example, a first coating may surround the first pH-adjusting substance and the active ingredient, and a second coating may surround the second pH-adjusting substance. The second coating may be designed to dissolve later than the first coating, or may be placed interior to the first coating and/or the active ingredient in the dosage form. After administration, the coatings control the sequential release of the dosage form's components to produce the desired sequential changes in the pH of the localized environment.

With respect to the nature of the coatings, any suitable coating may be used to control the release of the pH-adjusting substances, including, for example, enteric coatings, coatings responsive to pH changes, coatings which are metabolized by enzymes present specifically or predominantly in the localized environment of the target site of absorption, and coatings which dissolve after a certain period of time or after exposure to a certain volume of liquid, as well as any coatings known to those skilled in the art. The coating(s) may be applied to the entire dosage form or to a portion thereof; it may substantially surround the pH-adjusting substance(s), any one or more layers of a multilayered tablet, the individual particles or small aggregates. The nature and the thickness of the coating (s) may be used to control the times of release and the like. The thickness of the coatings may be regulated in any manner known to those skilled in the art.

Preferably, the active ingredient and the first pH-adjusting substance are uncoated to effect immediate release of the active ingredient from the dosage form. However, it may also be desired to provide a coating or coatings around the active ingredient and/or first pH-adjusting substance, for example, for taste-masking purposes or in delayed-release dosage forms. Also, the release of the active ingredient may have to be delayed, for example, during the passage of the dosage form through those segments of the gastro-intestinal tract that precede the desired site of absorption. For example, a coating surrounding the entire dosage form may be used to prevent a premature release of the active ingredient until the dosage form reaches the target site of absorption, e.g., duodenum, etc. Thus, a layered tablet may include the first pH-adjusting substance and the active ingredient located in a layer on the exterior of the tablet and being substantially encompassed by a first coating. The second pH-adjusting substance may be located interior to the active ingredient and first pH-adjusting substance, being substantially encompassed by a second coating.

Membranes may be also used to control the release of the pH-adjusting substances. For example, an active ingredient and a first pH-adjusting substance may be combined in a dosage form with a membrane and a second pH-adjusting substance. The active ingredient and the first pH-adjusting substance may be placed peripheral to the membrane. The second pH-adjusting substance may be placed interior to or surrounded by the membrane.

The pH-adjusting substances may also be sequentially released or activated by using one or more controlled release matrix materials. Suitable matrix materials include, for example, hydrophobic, plastic or hydrophilic matrix materials. Suitable examples of hydrophobic matrix materials are carnuba wax, stearyl alcohol, and hydrogenated castor oil. Suitable examples of plastic matrix materials are ethylcellulose and polyvinyl alcohol. Suitable examples of hydrophilic matrix materials are hydroxypropylcellulose, methylcellulose, hydroxypropyl methylcellulose, hydroxy ethylcellulose and hydroxypropyl ethylcellulose.

Preferably, when matrix materials are utilized, the pH-adjusting substances are located in different layers of a bi-layered or multi-layered tablet. For example, the first pH-adjusting substance and the active ingredient may be placed in the top and bottom outer layers of a 3-layered tablet, while the second pH-adjusting substance and the matrix material are placed in the middle layer. A coating may be used to keep the tablet substantially intact until it reaches the desired site of absorption. At the desired site, the active ingredient and the first pH-adjusting substance will be rapidly released, while the matrix material delays the release of the second pH-adjusting substance, for example for 10 minutes after the release of the outer layers, producing sequential pH adjustment. Alternatively, a portion of the active ingredient may be placed in each of the layers, or a smaller amount of the matrix material may also be placed in the outer layers.

The sequential adjustment of the localized environment may also be implemented by using precursors of the active ingredients and/or the pH-adjusting substances. The precursors of the active ingredients typically are neither basic nor acidic since a protecting group(s) is usually attached to the basic or acidic portion(s) of the molecule. The precursors, for example pro-drug compounds, typically convert to the active form in vivo after the administration of the precursor. The examples of such precursors include lactones, which usually convert to free acids via lactone ring opening, and esters, which convert to a free acid via de-esterification. In vivo, the protecting group(s) of the precursor compound is removed, producing a de-protected form of the active ingredient, which may now be more susceptible to pH adjustment or other dissolution and/or absorption-enhancing substances in the localized environment. Typically, the precursors are converted to the active or the de-protected form by enzymes, acids or bases.

Similarly, the pH-adjusting substances themselves may be utilized in the form of precursors and activated in the localized environment of the active ingredient. For example, a weakly basic active ingredient may be administered with the acidic first pH-adjusting substance and a precursor of the second pH-adjusting substance, which may be converted to a base upon de-protection. All three components may be administered in a dosage form and simultaneously released at the desired site. The first pH-adjusting substance lowers the pH of the localized environment, promotes the dissolution of the active ingredient and the activation of the second pH-adjusting substance (i.e., the conversion of the precursor to a base). In turn, the base produced by the conversion of the precursor, raises the pH and promotes the absorption of the active ingredient.

The materials and mechanisms for sequentially controlling the modification of the localized environment may be also combined. For example, a coating and a matrix material, a coating and a membrane, and similar combinations may be used in the same dosage form.

For various active ingredients, different factors may have to be taken into account when selecting the appropriate pH-adjusting system. For example, proteins and amino acids may exist as zwitterions, which reach their highest concentration at the so-called iso-electric point. Zwitterions have both negatively- and positively-charged functional groups, and commonly have the lowest solubility among other species of the same compound. Therefore, for compounds that form zwitterions, the isoelectric point of the compound may have to be considered in selecting the pH-adjusting system. Similarly, $pK_a$ of the active ingredient, bioavailability of the selected active ingredient, pH at the sites of absorption and/or administration, issues of active transport and many other factors may also be considered.

Active ingredients suitable for use in the present invention include systemically distributable pharmaceutical ingredients, vitamins, minerals, dietary supplements, as well as non-systemically distributable drugs. Pharmaceutical ingredients may include, without limitation, analgesics, anti-inflammatories, antipyretics, antibiotics, antimicrobials, laxatives, anorexics, antihistamines, antiasthmatics, antidiuretics, anti-flatulents, antimigraine agents, antispasmodics, sedatives, antihyperactives, antihypertensives, tranquilizers, decongestants, beta blockers; peptides, proteins, oligonucleotides and other bio-molecules, and combinations thereof. The term bio-molecules is defined as substances of biological origin that naturally occur in the living organisms, as well as synthetic analogs and modifications thereof.

Preferably, the active ingredients are drugs that display poor pharmacokinetic characteristics including low bioavailability, slow absorption or long $t_{max}$, including small molecule drugs, nutritional supplements (for example, vitamins), and proteins, peptides and other bio-molecules.

Table 1 shows some examples of suitable drugs and their bioavailability:

TABLE 1

| DRUG | BIOAVAILABILITY (%) |
|---|---|
| Benazepril:HCI | 37 |
| Moexipril | 13 |
| Enalapril | 41-60 |
| Doxazosin | 65 |
| Prazocin | 65 |
| Carvedilol | 25-35 |
| Propranolol:HCI | 26 |
| Nalbuphine | 16 (±8) |
| Butorphanol Tartrate (Nasal Spray) | 60%-70% |
| Granisetron:HCI | 60% |
| Ondansetron:HCI | 55 |

TABLE 1-continued

| DRUG | BIOAVAILABILITY (%) |
| --- | --- |
| Nicotine | 16.7 (±8.6%) |
| Bupropion:HCl (in animals) | 5%-20% |
| Bromocriptine | 28 |
| Ipratropium Bromide | 7 |
| Terbutaline sulphate | 30-70 |
| Finasteride | 63 |
| Labetalol | 18 ± 5 |
| Atenolol | 50 |
| Doxepin | 27 ± 10 |
| Quinapril•HCl | 60 |

The active ingredients having especially poor bioavailability when administered via the commonly known methods and formulation, especially weak acids and bases, are the most preferred candidates for administration in accordance with the invention.

The compositions of the present invention may be administered by any suitable transmucosal route of administration, for example, buccal, sublingual and gingival (by holding the dosage form in the mouth), gastrointestinal (by swallowing the dosage form), rectal (by inserting the composition into the rectum), vaginal (by inserting the composition into the vagina), and nasal (by applying the composition to the nasal cavity).

Many transmucosal routes of administration, including buccal, sublingual, gingival, rectal, and vaginal have the added advantage of avoiding loss of the active ingredient resulting from the effect of first pass metabolism by the liver or from metabolism in the gastrointestinal tract. Furthermore, although it is impractical and may not be desirable to change the pH of the entire contents of the small intestine, it is, nevertheless, possible to alter the pH of the local environment (intestinal contents in immediate contact with the dosage form and any active ingredient that may have dissolved from it) in accordance with the present invention.

The choice of the route of administration depends on many factors, including the pH at the site of absorption. Table 2 shows the approximate pH values for various body cavities and tissues:

TABLE 2

| BODY CAVITY | pH |
| --- | --- |
| ESOPHAGUS | 5-6 |
| STOMACH | 1-3.5 |
| DUODENUM | 5-6.8 |
| JEJENUM | 6-7 |
| ILEUM | 6.5-7.5 |
| LARGE INTESTINE | 5.5-7 |
| CAECUM | ~5.7 |
| COLON | 6.4-7.5 |
| RECTUM | ~6.7 |
| VAGINA | 4-5.5 |
| NASAL | 5.1-8 |
| BUCCAL, ORAL, SUBLINGUAL | ~7 |

Preferably, the body cavity having a physiological pH range that is close to the desired pH range for the active ingredient as defined in the invention is preferred. Most preferably, the $pK_a$ of the desired active ingredient falls within the pH range of the selected body cavity. For example, as described above, it is desirable to minimize the pH adjustment to reduce tissue irritation. Thus, the choice of the body cavity with a pH that does not require a large pH adjustment to effect dissolution and/or absorption may reduce the likelihood of tissue irritation.

Therefore, different sites of absorption and/or administration are preferred for different active ingredients. For example, the esophagus (pH=5-6) has a more acidic pH than the oral cavity (pH=7). Thus, the desired dissolution of an acidic drug with a $pK_a$ of 5 in the esophagus would require a smaller first pH adjustment than the dissolution of the same drug within the oral cavity.

Illustrating, Apomorphine ($pK_a$=7) is suited to administration in the oral cavity (pH=7). The first pH adjustment to approximately 6 may be followed by the second pH adjustment to approximately pH 8, with both Apomorphine's $pK_a$ and the initial pH of the body cavity being in the middle of the adjustment range. Papaverine ($pK_a$=5.9) is suited for a vaginal administration (pH=4-5.5). The adjustments of one pH unit above and below Papaverine's $pK_a$ are not likely to cause significant tissue irritation. Bromocriptine ($pK_a$=4.9) is also suitable for vaginal administration.

Preferably, the compositions of the invention are administered in a form suitable for delivery to the selected site of administration. Suitable dosage forms include, for example, tablets, granules, pellets, multiparticulates, capsules, minitablets, beads, powders, suppositories, gels, and solutions, liquid drugs, emulsions, microemulsions. In general, the dosage forms may be prepared by mixing the ingredients using techniques well known to those skilled in the art.

If tablets are used, the tablets may be matrix tablets, layered tablets in which the various components are separated in different layers, or other specialized forms of tablets, including non-conventional shapes and geometric arrangements. Direct compression, wet granulation or any other tablet manufacturing technique known in the art may be utilized to manufacture the tablets. See, e.g., U.S. Pat. Nos. 5,178,878 and 5,223,264, which are incorporated by reference herein. Excipient fillers may be used to facilitate tableting. Fillers desirably will also assist in the rapid dissolution of the dosage form. Non-limiting examples of suitable fillers include mannitol, dextrose, lactose, and sucrose.

Pellets or other multi-particulate dosage forms or formulations may be manufactured by granulation, layering techniques, extrusion and spheronization or other pellet manufacturing methods. Wet or dry granulation processes may be used to make granules.

Any suitable capsule known in the art may be used, including, for example, soft gelatin capsules, hard gelatin capsules and variations thereof. Starch capsules or capsules made of other suitable materials may also be used. The capsules may be filled with a loose powder consisting of various components suitably mixed, or a slightly compressed slug of powdered material. Suitable fillers, diluents, flow promoting agents, and lubricants may be included. Diluents may include for example lactose, mannitol, sucrose, dextrose, microcrystalline cellulose and sorbitol. Flow promoting agents may include, for example, silicon dioxide and talc. The examples of suitable lubricants include magnesium stearate, stearic acid and glyceryl behenate.

Pellets, granules and minitablets may also be used to fill the capsules. Optionally, a capsule may contain a fill consisting of more than one component, for example, minitablets and powder. The powder may contain the first pH-adjusting substance and the active ingredient, whereas the tablet may contain the second pH-adjusting substance.

Administration may be carried out by means of a liquid, liquid/solid or a powder solution. For example, a liquid may be supplied as a powder for reconstitution by the addition of a predetermined volume of water or other liquid that may be co-packaged with the powder. The powder and liquid are mixed immediately before administration. In this way, the first pH-adjusting substance is immediately available (upon reconstitution), whereas the second pH-adjusting system is released at some later time point, as determined by the formulator. Liquid formulations preferably contain viscosity enhancers and bioadhesives.

For vaginal administration, tablets may be used, and prepared as described above. The tablets may, optionally, have special shapes to assist insertion of the compressed dosage form. These shapes include oval, capsule-shaped, and diamond-shaped tablets. An applicator device may also be supplied with the tablets to make insertion easier and to facilitate insertion deep into the vaginal cavity. Such applicators are commonly used in the pharmaceutical industry for this purpose.

Vaginal and rectal administration may also be achieved by means of suppositories. These are solid, molded units that are formed by pouring into suitable molds a molten wax or fatty material or other suitable substance, as the base, into which the drug is dissolved or dispersed, pH-adjusting substances, optional additional penetration enhancers and other excipients. Upon cooling, the base forms a solid containing the drug and other dispersed ingredients. On solidification, the base takes the shape of the mold. Examples of bases that could be used are cocoa butter, polyethylene glycols, polyvinyl pyrrolidone, gelatin, gelatin/glycerin combinations, esterfied fatty acids, polyoxyethylene sorbitans and polyoxyethylene sorbitan fatty acid esters. Various additives may be incorporated including surfactants and absorption enhancers such as medium chain (C8 to C12) fatty acids and fatty acid esters including mono-, di-, and triesters of glycerol. Various proprietary bases which may contain mixtures of different components are also available. Examples of proprietary bases are those sold under the trade names Imhausen, Witepsol and Gelucire. Various grades of each of these are available for specific applications. Mixtures of various bases may also be utilized in order to obtain a suppository with the required properties. Other shaping methods for forming the suppositories including cold molding and compression may also be used.

For delivery of an active ingredient to the esophagus, for example, a tablet or powder for reconstitution containing an immediate release pH-adjusting substance and slowly released pH-adjusting substance suspended as a fine powder in the liquid are preferred. The liquid may contain water, preservatives to prevent microbial growth, surfactants, viscosity enhancers, mucoadhesives and additional organic solvents. Nonlimiting examples of preservatives are methylparaben and propylparaben used in a concentration, respectively of 0.02% and 0.002%. Some of the active ingredient and other components may rapidly traverse the length of the esophagus and pass into the stomach. In an appropriately formulated and administered system, however, a major portion of the active ingredient and pH-adjusting substances are retained on the wall of the esophagus where the sequential pH-adjusting system promotes the absorption of the drug through the esophageal lining. Appropriate administration occurs when the viscous liquid is slowly given into the back of the mouth by means of, for example, a medicine measure inserted deep into the mouth, and more particularly a pipette-type dropper (as used for the administration of liquids to children), or a wide diameter drinking straw each of which is inserted into the back of the mouth. This mode of administration decreases retention of the composition in the mouth as well as preventing extensive dilution of the composition with saliva.

For nasal administration, solutions similar to those described for the esophagus are preferably employed. The solutions preferably include bioadhesive and viscosity enhancing agents. For purposes of this invention, nasal gels are considered as solutions with larger amounts of viscosity enhancing agents. Viscosity enhancing agents include, for example, alginates, chitosan, starches, and celluloses.

For absorption through the duodenum, jejunum and ileum and other similar areas of the gastrointestinal tract, the dosage form should have an enteric coating. Suitable enteric coatings include, for example, a coating which is insoluble in acidic gastric juice but soluble in alkaline digestive juice. Such a coating enables the intact dosage form to pass through the stomach into the duodenum, etc., from where the drug is absorbed. Suitable enteric coatings include, for example, cellulose acetate phthalate. Alternatively, other enteric polymers known in the art can be used, such as cellulose acetate trimellitate, hydroxypropyl methylcellulose phthalate, hydroxypropyl methylcellulose acetate succinate, shellac, carboxymethylethylcellulose or polyvinylacetate phthalate (sold under the Trademarks Opadry Aqueous Enteric and Opadry Enteric). The coating can be done in any conventional manner using, for example, a pH dependent polymer so as to form a pH responsive dosage form.

For the large intestine, the product may contain enteric materials or be combined in a matrix of material that only degrades in the large intestine, e.g., bacteria present only in the colon will break down the material.

Although the sequential pH-adjusting systems are preferably used for immediate release dosage forms, the sequential pH-adjusting systems may also be used for various controlled release dosage forms. As used in this context, a controlled release dosage form is one in which the release of the active ingredient is controlled from about 1 to about 2 minutes to several hours, relative to the release of the active ingredient from a regular (noncontrolled release) dosage form of similar properties. More commonly, for administration in the oral cavity, controlled release will occur from 3 to 60 minutes after administration, whereas controlled release in a rectal dosage form would occur from 5 to 40 minutes. As used in this context, "immediate release" means that the dosage form does not contain any intentionally engineered mechanisms for controlling the release of the active ingredient, i.e., the particles of the active ingredient are not coated or contained within a matrix, for example, to control the release of the active ingredient. The active ingredient is released as soon as, for example, the tablet disintegrates or the suppository melts or dissolves, etc. In the sequential pH-adjusting systems presently described, the release of a pH-adjusting substance may be delayed without detracting from this definition of an immediate release dosage form. "Immediate release" in the context of an immediate release dosage form refers to the release of the active ingredient.

The dosage form may also contain agents useful for delivery of an active ingredient to the selected target site of absorption and to aid in penetration of biological tissues. For example, depending on the dosage form and the target site of absorption, other materials or techniques may be used with the present dosage forms to enhance dissolution and absorption, to improve the disintegration profile, and/or to improve the organoleptic properties, when suitable. These include, but are not limited to, the use of disintegration agents; chemical penetration enhancers; adsorption of the drug on to fine particles to promote absorption by specialized cells within the gastrointestinal tract; ion pairing or complexation; and the use of lipids and/or surfactants.

The selected enhancement technique is preferably related to the route of drug absorption, i.e., paracellular or transcellular and the site of absorption. The materials used to enhance dissolution and absorption, etc., may also be sequentially released or made active at different times in combination with the pH-adjusting substances of the present invention. For example, dissolution enhancing ingredients may be released with the first pH-adjusting substance and absorption enhancing ingredients may be released with the second pH-adjusting substance.

Nonlimiting examples of suitable disintegration agents include, for example, microcrystalline cellulose, croscarmelose sodium, crospovidone, starches, corn starch, potato starch and modified starches thereof, and clays, such as bentonite, alginates, gums such as agar, guar, locust bean, karaya, pecitin and tragacanth.

A bioadhesive may also be included in the dosage form to increase the area of contact between, and the residence time of, the dosage form at the site of administration or absorption. Nonlimiting examples of bioadhesives used in the present invention include, for example, Carbopol 934 P, Na CMC, Methocel, Polycarbophil (Noveon AA-1), HPMC, Na alginate, Na Hyaluronate and other natural or synthetic bioadhesives.

Penetration enhancers may also be included in the dosage form to improve absorption. For example, a second portion of the dosage form may include a second pH-adjusting substance and/or a penetration enhancer in an enteric coating. After the first portion promotes dissolution of the active ingredient, the enteric coating dissolves, releasing the penetration enhancer, which may be more stable or more effective at the pH necessary to promote absorption than at the pH necessary to promote the dissolution of the active ingredient. Non-limiting examples of penetration enhancers include effervescent couples (e.g., sodium bicarbonates/citric anhydride combination), bile salts, sodium salicylase, aprotinin, glyceride and the like.

The dosage forms may also include glidants, lubricants, binders, excipients and the like, when appropriate. Examples of binders which can be used include povidone, acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like.

In addition, if the dosage form is intended for oral administration, the dosage forms may also include sweeteners, flavoring and coloring components. Any conventional sweetener or flavoring component may be used. Combinations of sweeteners, flavoring components, or sweeteners and flavoring components may likewise be used. Coloring agents may include titanium dioxide, and dyes suitable for food such as those known as F.D.& C. dyes and natural coloring agents such as grape skin extract, beet red powder, beta-carotene, annatto, carmine, turmeric, paprika, etc. Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds and cassia oil. Also useful as flavors are vanilla, citrus oil, including lemon, orange, grape, lime, and grapefruit, and fruit essences, including apple, pear, peach, strawberry, raspberry, cherry, plum, pineapple, apricot and so forth.

Flavors that have been found to be particularly useful include commercially available orange, grape, cherry and bubble gum flavors and mixtures thereof. The amount of flavoring may depend on a number of factors, including the organoleptic effect desired.

Various penetration enhancers may also be used including bile salts and their derivatives (e.g., taurocholate, deoxycholate, and glycocholate); chelators (e.g., citric acid, enamines, EDTA); fatty acids and their derivatives (e.g., arachidonic acid, oleic acid, sodium caprylate, monoolein); surfactants (e.g., SDS, polyoxyethylene-20-cetylether); and nonsurfactants (e.g., 1-alkylazacycloalkanone unsaturated ureas).

The preferred embodiment of the invention described above relates primarily to the modification of the localized environment via pH control. However, other mechanisms of adjustment are also contemplated. For example, presence of penetration enhancers may promote absorption. The effervescent penetration enhancers are especially effective in this regard. Similarly, non-effervescent penetration enhancers, hydrophobic modifiers, and the like may also be used to promote absorption. Likewise, dissolution may be promoted by various additives, such as pharmaceutically acceptable crown ethers, various complexing agents, liposome compounds, polyalkoxy derivatives such PEG and PPG compounds and the like.

To illustrate, according to one embodiment of the invention, a first enteric coating may envelop the dosage form, which may include a first portion and a second portion interior to the coating. The first portion of the dosage form may include a major part of the active ingredient and a dissolution enhancer. The second portion of the dosage form may include the rest of the active ingredient and an effervescent penetration enhancer in a second enteric coating. At the desired site, the first enteric coating dissolves and releases most of the active ingredient and the dissolution enhancer, which promotes dissolution. The dissolution enhancer may include for example a pH-adjusting substance, a PEG derivative of the active ingredient and the like. Thereafter, the second enteric coating dissolves, releasing the balance of the active ingredient and the effervescent couple, which promotes absorption of the active ingredient across the mucosal membrane.

The following non-limiting prophetic examples are included herein for the purpose of illustration.

PROPHETIC EXAMPLE ONE

Saquinavir Mesylate

Saquinavir ($pK_a=7$) is metabolized in the gut and in the liver. The oral transmucosal administration of Saquinavir (buccal or sublingual delivery) avoids the first pass metabolism and is therefore preferred. Table 3 shows a formulation of Saquinavir mesylate for oral transmucosal administration. The formulation of Table 3 includes a pH-adjusting system for sequential pH adjustment of the localized environment of Saquinavir mesylate:

TABLE 3

| COMPONENT | QUANTITY |
| --- | --- |
| Saquinavir mesylate | 50 mg |
| Lactose (direct compression grade) | 103 mg |
| Avicel PH 102 | 100 mg |
| Citric Acid | 1 mg |
| Coated Sodium Bicarbonate | 3 mg |
| Explotab ® | 6 mg |

TABLE 3-continued

| COMPONENT | QUANTITY |
| --- | --- |
| Silicon dioxide | 4 mg |
| Magnesium Stearate | 3 mg |

Sodium bicarbonate is coated with the solution shown in Table 4 to a weight gain of 4%:

TABLE 4

| COMPONENT | QUANTITY |
| --- | --- |
| Hydroxypropylmethyl cellulose phtalate | 418.5 g |
| Triethylcitrate | 31.5 g |
| Ethanol | 2025 g |
| Acetone | 2025 g |
| TOTAL | 4500 g |

All ingredients apart from magnesium stearate are blended for 20 minutes. Magnesium stearate is added and the mixture blended for a further 5 minutes. The blend is directly compressed into tablets, each weighing 270 mg.

PROPHETIC EXAMPLE 2

Bromocryptine for Vaginal Administration

Table 5 shows a formulation of Bromocryptine that includes a sequential pH-adjusting system:

TABLE 5

| COMPONENT | QUANTITY |
| --- | --- |
| Bromocryptine | 5 mg |
| Citric acid | 3 mg |
| Coated Sodium Bicarbonate | 9 mg |
| Lactose | 300 mg |
| Avicel PH 101 | 100 mg |
| Magnesium stearate | 5 mg |
| Silicon dioxide | 4 mg |
| Sodium starch glycolate | 4 mg |

Sodium bicarbonate is coated to a weight gain of 5% with the solution described in Table 4. All ingredients except magnesium stearate are blended in an V-blender for twenty minutes. Then, magnesium stearate is added to the blender and the mixture is blended for an additional five minutes. Diamond-shaped punches are used to compress the blend to a hardness of 40-50N, producing diamond-shaped tablets for vaginal administration.

PROPHETIC EXAMPLE 3

Prochloroperazine For Rectal administration

Table 6 shows a formulation of Prochloroperazine for rectal administration:

TABLE 6

| COMPONENT | QUANTITY |
| --- | --- |
| Prochloroperazine | 6 mg |
| NaHPO$_4$ | 2 mg |
| Coated Sodium Carbonate | 9 mg |
| Polyethylene glycol 4000 | 1100 mg |
| Polyethylene glycol 1000 | 383 mg |

Sodium Carbonate is coated with the solution of Table 4 to a 5% weight gain. Polyethylene glycol 4000 is melted. Polyethylene glycol 1000 is added to the melt and the mixture is gently heated to maintain the molten state. All other ingredients are added into the molten mixture with stirring and mixed throughout. The melt is then poured into 1.5 g molds to produce Prochloroperazine suppositories for rectal administration.

Unless stated to the contrary, any use of the words such as "including," "containing," "comprising," "having" and the like, means "including without limitation" and shall not be construed to limit any general statement that it follows to the specific or similar items or matters immediately following it. References to a "plurality" of things mean at least two of the things.

Except where the context indicates to the contrary, all exemplary values are intended to be fictitious, unrelated to actual entities and are used for purposes of illustration only.

Most of the foregoing alternative embodiments are not mutually exclusive, but may be implemented in various combinations to achieve unique advantages. As these and other variations and combinations of the features discussed above can be utilized without departing from the invention as defined by the claims, the foregoing description of the embodiments should be taken by way of illustration rather than by way of limitation of the invention as defined by the appended claims.

What is claimed is:

1. A pharmaceutical composition comprising an active ingredient in a dosage form comprising a first portion, a second portion and means for sequential release of said first portion and said second portion at a desired site within a subject; wherein the desired site is one of the duodenum, jejunum, ileum, large intestine, caecum, colon, rectum, vagina, nasal cavity, esophagus, stomach, buccal region, oral cavity, and sublingual region;

said first portion comprising one or more first pH-adjusting substance for adjusting a localized environment of said active ingredient at said desired site to promote dissolution of said active ingredient; said second portion comprising one or more second pH-adjusting substance for adjusting said localized environment of said active ingredient at said desired site to promote absorption of said active ingredient; and wherein said means for sequential release comprise means for sequentially controlling the activity of said pH-adjusting substances so that said first pH-adjusting substance attains peak activity in the localized environment of the active ingredient before said second pH-adjusting substance attains peak activity in the localized environment, whereby the localized environment of the active ingredient attains a first pH and then a second pH;

wherein said means for sequentially controlling the activity of said pH-adjusting substances comprises at least one coating that surrounds said second pH-adjusting substance; said first pH-adjusting substance being peripheral to said coating;

and wherein said active ingredient is peripheral to said coating in said dosage form.

2. A pharmaceutical composition comprising an active ingredient in a dosage form comprising a first portion, a second portion and means for sequential release of said first portion and said second portion at a desired site within a subject; wherein the desired site is one of the duodenum, jejunum, ileum, large intestine, caecum, colon, rectum, vagina, nasal cavity, esophagus, stomach, buccal region, oral cavity, and sublingual region;

said first portion comprising one or more first pH-adjusting substance for adjusting a localized environment of said active ingredient at said desired site to promote dissolution of said active ingredient; said second portion comprising one or more second pH-adjusting substance for adjusting said localized environment of said active ingredient at said desired site to promote absorption of said active ingredient; and wherein said means for sequential release comprise means for sequentially controlling the activity of said pH-adjusting substances so that said first pH-adjusting substance attains peak activity in the localized environment of the active ingredient before said second pH-adjusting substance attains peak activity in the localized environment; whereby the localized environment of the active ingredient attains a first pH and then a second pH;

wherein said means for sequentially controlling the activity of said pH-adjusting substances comprises a controlled release matrix material in said dosage form, said second pH-adjusting substance being dispersed in said controlled release matrix material, and said first pH-adjusting substance being peripheral to said controlled release matrix material;

and wherein said active ingredient is peripheral to said matrix material in said dosage form.

3. A pharmaceutical composition comprising an active ingredient in a dosage form comprising a first portion, a second portion and means for sequential release of said first portion and said second portion at a desired site within a subject; wherein the desired site is one of the duodenum, jejunum, ileum, large intestine, caecum, colon, rectum, vagina, nasal cavity, esophagus, stomach, buccal region, oral cavity, and sublingual region;

said first portion comprising one or more first pH-adjusting substance for adjusting a localized environment of said active ingredient at said desired site to promote dissolution of said active ingredient; said second portion comprising one or more second pH-adjusting substance for adjusting said localized environment of said active ingredient at said desired site to promote absorption of said active ingredient;

and wherein said means for sequential release comprise means for sequentially controlling the activity of said pH-adjusting substances so that said first pH-adjusting substance attains peak activity in the localized environment of the active ingredient before said second pH-adjusting substance attains peak activity in the localized environment, whereby the localized environment of the active ingredient attains a first pH and then a second pH;

wherein said means for sequentially controlling the peak activities of said pH-adjusting substances comprises at least one membrane in said dosage form that surrounds said second pH-adjusting substance, said first pH-adjusting substance being peripheral to said membrane; wherein said active ingredient is peripheral to said membrane in said dosage form.

4. The pharmaceutical composition of any one of claims 1, 2 and 3, wherein said first and second pH-adjusting substances are respectively an acid and a base.

5. The pharmaceutical composition of any one of claims 1, 2 and 3, wherein said first and said second pH-adjusting substances are respectively a base and an acid.

6. The pharmaceutical composition of any one of claims 1, 2 and 3, wherein said first and said second pH-adjusting substances are respectively a base and a base.

7. The pharmaceutical composition of any one of claims 1, 2 and 3, wherein said first and second pH-adjusting substances are respectively an acid and an acid.

8. The pharmaceutical composition of any one of claims 1, 2 and 3, wherein said means for sequential release further comprises means selected from the group consisting of active ingredients pre-cursors, precursors of pH-adjusting substances and mixtures thereof.

9. The pharmaceutical composition of any one of claims 1, 2 and 3, wherein said active ingredient is selected from the group consisting of analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers, peptides, proteins, and oligonucleotides.

10. The pharmaceutical composition of any one of claims 1, 2 and 3, wherein said first portion further comprises one or more first substances selected from the group consisting of pH-adjusting substances, surface-active compounds, pharmaceutically-acceptable solvents and enveloping additives, and said second portion further comprises one or more substances selected from the group consisting of effervescent penetration enhancers, non-effervescent penetration enhancers, enzymes and bioadhesives.

11. The pharmaceutical composition of claim 8, further comprising a substance selected from the group consisting of enzymes, acids and bases in order to convert said precursors to an active form.

* * * * *